United States Patent
Plos et al.

(10) Patent No.: US 6,685,750 B1
(45) Date of Patent: Feb. 3, 2004

(54) COMPOSITION FOR THE OXIDATION DYEING OF KERATIN FIBERS AND DYEING PROCESS USING THIS COMPOSITION

(75) Inventors: Grégory Plos, Paris (FR); Sylvain Kravtchenko, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/586,931

(22) Filed: Jun. 5, 2000

(30) Foreign Application Priority Data

Jun. 4, 1999 (FR) .............................. 99 07092

(51) Int. Cl.$^7$ ................................ A61K 7/13
(52) U.S. Cl. .................... 8/405; 8/401; 8/405; 8/406; 8/410; 8/411
(58) Field of Search ................. 8/401, 405, 406, 8/410, 411

(56) References Cited

U.S. PATENT DOCUMENTS

| | | | |
|---|---|---|---|
| 4,003,699 A | | 1/1977 | Rose et al. .................. 8/10.2 |
| 4,823,985 A | | 4/1989 | Grollier et al. ................. 222/1 |
| 5,061,289 A | | 10/1991 | Clausen et al. ................ 8/405 |
| 5,380,340 A | | 1/1995 | Neunhoeffer et al. .......... 8/409 |
| 5,538,517 A | * | 7/1996 | Samain et al. ................. 8/423 |
| 5,766,576 A | | 6/1998 | Löwe et al. .................. 424/62 |
| 5,769,903 A | * | 6/1998 | Audousset et al. ............. 8/409 |
| 5,899,212 A | * | 5/1999 | Sorensen et al. .............. 8/401 |
| 6,270,534 B1 | * | 8/2001 | de la Mettrie et al. ......... 8/406 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| DE | 197 13 852 | 10/1998 |
| EP | 0 310 675 | 4/1989 |
| EP | 0 770 375 | 5/1997 |
| FR | 2 586 913 | 3/1987 |
| FR | 2 733 749 | 11/1996 |
| FR | 2 750 048 | 12/1997 |
| GB | 1 026 978 | 4/1966 |
| GB | 1 153 196 | 5/1969 |
| GB | 1 320 250 | 6/1973 |
| JP | 5-163124 | 6/1993 |
| WO | WO 94/00100 | 1/1994 |
| WO | WO 94/08969 | 4/1994 |
| WO | WO 94/08970 | 4/1994 |
| WO | WO-9425574 | * 11/1994 |
| WO | WO 96/15765 | 5/1996 |
| WO | WO 97/41215 | 11/1997 |
| WO | WO 99/15137 | 4/1999 |

OTHER PUBLICATIONS

English language Derwent Abstract of DE 197 13 852. Oct. 1998.
English language Derwent Abstract of EP 0 770 375. May 1997.
English language Derwent Abstract of FR 2 733 749. Nov. 1996.
English language Derwent Abstract of FR 2 750 048. Jun. 1997.
English language Derwent Abstract of JP 5–163124. Jun. 1993.

* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett & Dunner, L.L.P.

(57) ABSTRACT

A ready-to-use composition for the oxidation dyeing of keratin fibers, and, in particular, human keratin fibers such as the hair, including at least one oxidation base, at least one ammonia-generating 2-electron oxidoreductase type enzyme, and at least one donor for the enzyme, as well as a dyeing process using this composition.

46 Claims, No Drawings

COMPOSITION FOR THE OXIDATION DYEING OF KERATIN FIBERS AND DYEING PROCESS USING THIS COMPOSITION

A subject of the invention is a composition for the oxidation dyeing of keratin fibers, and, in particular, human keratin fibers, such as the hair, comprising, in a medium suitable for dyeing, at least one oxidation base, at least one ammonia-generating 2-electron oxidoreductase type enzyme, and at least one donor for the enzyme, as well as the dyeing process using this composition.

It is known to dye keratin fibers, and, in particular, human hair, with dye compositions containing oxidation dye precursors, in particular, ortho- or para-phenylene-diamines, ortho- or para-aminophenols and heterocyclic bases, generally referred to as oxidation bases. Oxidation dye precursors, or oxidation bases, are colorless or weakly colored compounds that, when combined with oxidizing products, can give rise to colored compounds and dyes by a process of oxidative condensation.

It is also known that the shades obtained with these oxidation bases can be varied by combining them with couplers or color modifiers, the latter being chosen, in particular, from aromatic meta-diamines, meta-aminophenols, meta-diphenols and certain heterocyclic compounds.

The variety of molecules used as the oxidation bases and the couplers allows a wide range of colors to be obtained.

The so-called "permanent coloration" obtained through these oxidation dyes should, moreover, satisfy a certain number of desired properties. Desirably, there should be no toxicological drawbacks, shades of the desired intensity to be obtained, and the dyes should be able to,withstand external agents, e.g., light, bad weather, washing, permanent waving, perspiration, and/or rubbing.

Desirably, the dyes should also be able to cover white hair and, lastly, they should be as unselective as possible, i.e., they should give the smallest possible color differences along the same length of keratin fiber, which may in fact be differently sensitized, i.e., damaged, between its tip and its root.

The oxidation dyeing of keratin fibers is generally carried out in strongly alkaline medium, in the presence of hydrogen peroxide. However, the use of alkaline media in the presence of hydrogen peroxide has the drawback of causing appreciable degradation of the fibers, as well as bleaching of the keratin fibers, which is not always desirable.

The oxidation dyeing of keratin fibers can also be carried out using oxidizing systems other than hydrogen peroxide, such as enzymatic systems. Thus, it has already been proposed to dye keratin fibers, in particular, in European patent application EP-A-0,310,675, the disclosure of which is incorporated herein by reference, with compositions comprising a benzene-type oxidation dye precursor in combination with enzymes, such as pyranose oxidase, glucose oxidase or uricase, in the presence of a donor for the enzymes. Although being used under conditions not resulting in degradation of the keratin fibers, comparable to that caused by the dyes used in the presence of hydrogen peroxide, these dyeing processes are not entirely satisfactory, in particular, regarding the intensity of the colorations obtained. The problem of the lack of solubility of the donor is also sometimes posed, which is the case, in particular, for uric acid, the donor corresponding to uricase.

The inventors have discovered that it is possible to obtain novel dyes, capable of leading to colorations that are more intense than those of the prior art using an enzymatic system, by combining at least one oxidation base, at least one ammonia-generating 2-electron oxidoreductase-type enzyme, and at least one donor for the enzyme.

This discovery forms the basis of the present invention.

A first subject of the invention is thus a ready-to-use composition for the oxidation dyeing of keratin fibers, and, in particular, human keratin fibers, such as the hair, characterized in that it comprises, in a medium suitable for dyeing:

at least one oxidation base, at least one ammonia-generating 2-electron oxidoreductase-type enzyme, and at least one donor for the enzyme.

The dye composition according to the invention makes it possible to obtain colorations that are more intense than those obtained with the compositions of the prior art using an enzymatic oxidizing system, such as, for example, the uric acid/uricase oxidizing system.

In addition, the colorations obtained with the dye composition according to the invention may be relatively unselective, and may stand up well to the various attacking factors to which the hair may be subjected, e.g., light, bad weather, washing, permanent-waving, etc.

A subject of the invention is also a process for the oxidation dyeing of keratin fibers using this ready-to-use dye composition.

According to the invention, the term ammonia-generating means: which releases ammonia gas or aqueous ammonia during the enzyme-donor reaction.

The nature of the oxidation base(s) used in the ready-to-use dye composition is not critical. It (they) can be chosen, for example, from para-phenylenediamines, double bases, para-aminophenols, ortho-aminophenols and heterocyclic oxidation bases.

Examples of para-phenylenediamines that can be used as oxidation base in the dye compositions according to the invention include the compounds of formula (I) below, and the acid addition salts thereof:

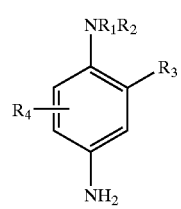

(I)

in which:

$R_1$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical, a $C_1$–$C_4$ alkyl radical substituted with a nitrogenous group, a phenyl radical and a 4'-aminophenyl radical;

$R_2$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical and a $C_1$–$C_4$ alkyl radical substituted with a nitrogenous group;

$R_3$ is chosen from a hydrogen atom, a halogen atom, such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino($C_1$–$C_4$) alkoxy radical, a $C_1$–$C_4$ mesylaminoalkoxy radical and a carbamoylamino($C_1$–$C_4$)alkoxy radical, $R_4$ is chosen from a hydrogen atom, a halogen atom and a $C_1$–$C_4$ alkyl radical.

Particular examples of the nitrogenous groups of formula (I) above include amino, mono($C_1$–$C_4$)alkylamino, di($C_1$–$C_4$)alkylamino, tri($C_1$–$C_4$)alkylamino, monohydroxy ($C_1$–$C_4$)alkylamino, imidazolinium and ammonium radicals.

More particular examples of the para-phenylenediamines of formula (I) above include para-phenylenediamine, para-tolylenediamine, 2-chloro-para-phenylenediamine, 2,3-dimethyl-para-phenylenediamine, 2,6-dimethyl-para-phenylenediamino, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediarmine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

The most particularly preferred examples of the para-phenylenediamines of formula (I) above include para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

According to the invention, the term double bases is understood to refer to the compounds containing at least two aromatic nuclei bearing amino and/or hydroxyl groups.

Particular examples of the double bases that can be used as oxidation bases in the dye compositions according to the invention include the compounds of formula (II) below, and the acid addition salts thereof:

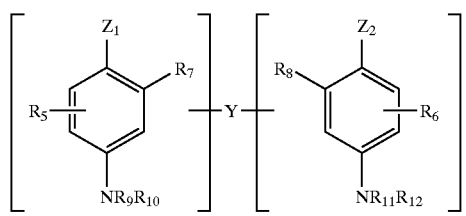

(II)

in which:
Z$_1$ and Z$_2$, which are identical or different, are chosen from a hydroxyl radical and an —NH$_2$ radical which is unsubstituted or substituted with a $C_1$–$C_4$ alkyl radical or with a linker arm Y;
the linker arm Y is a linear or branched alkylene chain containing from 1 to 14 carbon atoms, which is optionally interrupted by or terminated with one or more nitrogenous groups and/or one or more hetero atoms such as oxygen, sulphur or nitrogen atoms, and optionally substituted with one or more hydroxyl or $C_1$–$C_6$ alkoxy radicals;
R$_5$ and R$_6$ are chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical and a linker arm Y;
R$_7$, R$_8$, R$_9$, R$_{10}$, R$_{11}$ and R$_{12}$, which are identical or different, are chosen from a hydrogen atom, a linker arm Y and a $C_1$–$C_4$ alkyl radical;
it being understood that the compounds of formula (II) contain only one linker arm Y per molecule.

Particular examples of the nitrogenous groups of formula (II) above include amino, mono($C_1$–$C_4$)alkylamino, di($C_1$–$C_4$)alkylamino, tri($C_1$–$C_4$)alkylamino, monohydroxy ($C_1$–$C_4$)alkylamino, imidazolinium and ammonium radicals.

More particular examples of the double bases of formula (II) above include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-amino-phenyl)tetramethylenediamine, N,N'-bis(β-hydroxyethyl)-N,N'-bis(4-aminophenyl)-tetramethylenediamine, N,N'-bis(4-methylaminophenyl) tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid addition salts thereof.

Particularly preferred examples of double bases of formula (II) include N,N'-bis(β-hydroxyethyl)-N,N'-bis(4'-aminophenyl)-1,3-diaminopropanol and 1,8-bis(2,5-diaminophenoxy)-3,5-dioxaoctane, or one of the acid addition salts thereof.

Particular examples of the para-aminophenols that can be used as oxidation bases in the dye compositions according to the invention include the compounds of formula (III) below, and the acid addition salts thereof:

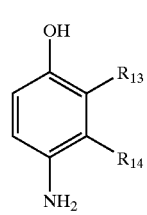

(III)

in which:
R$_{13}$ is chosen from a hydrogen atom, a halogen atom, a $C_1$–$C_4$ alkyl radical, a $C_1$–$C_4$ monohydroxyalkyl radical, a ($C_1$–$C_4$)alkoxy($C_1$–$C_4$)alkyl radical, a $C_1$–$C_4$ aminoalkyl radical and a hydroxy($C_1$–$C_4$)alkylamino ($C_1$–$C_4$)alkyl radical, R$_{14}$ is chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical, a $C_1$–$C_4$ cyanoalkyl radical and a ($C_1$–$C_4$)alkoxy($C_1$–$C_4$)alkyl radical, it being understood that at least one of the radicals R$_{13}$ or R$_{14}$ is a hydrogen atom.

Particular examples of the para-aminophenols of formula (III) above include para-aminophenol, 4-amino-3-methylphenol, 4-amino-3-fluorophenol, 4-amino-3-hydroxymethyl phenol, 4-amino-2-methyl phenol, 4-amino-2-hydroxymethylphenol, 4-amino-2-methoxymethylphenol, 4-amino-2-aminomethylphenol, 4-amino-2-(β- hydroxyethyl-aminomethyl)phenol and 4-amino-2-fluorophenol, and the acid addition salts thereof.

More particular examples of the ortho-aminophenols that can be used as oxidation bases in the dye compositions according to the invention include 2-aminophenol, 2-amino-5-methylphenol, 2-amino-6-methylphenol and 5-acetamido-2-aminophenol, and the acid addition salts thereof.

More particular examples of the heterocyclic bases that can be used as oxidation bases in the dye compositions according to the invention include pyridine derivatives, pyrimidine derivatives and pyrazole derivatives, and the acid addition salts thereof.

Among the pyridine derivatives, more particular examples of the compounds include those described, for example, in British patents GB 1,026,978 and GB 1,153,196, the disclosures of each of which are incorporated herein by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-di-aminopyridine, and the acid addition salts thereof.

Among the pyrimidine derivatives, more particular examples of the compounds include those described, for example, in German patent DE 2,359,399; Japanese patents JP 88-169,571; JP 05,163,124; European patent EP 0 770 375 or International patent application WO 96/15765, the disclosures of each of which are incorporated herein by reference, such as 2,4,5,6-tetraaminopyrimidine, 4-hydroxy-2,5,6-triaminopyridine, 2-hydroxy4,5,6-triaminopyrimidine, 2,4-dihydroxy-5,6-diaminopyrimidine and 2,5,6-triaminopyrimidine, and pyrazolopyrimidine derivatives, such as those mentioned in French patent application FR-A-2,750,048, the disclosure of which is incorporated herein by reference, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo [1,5-a] pyrimidin-7-ylamino)ethanol, 2-7(7-aminopyrazolo [1,5-a]pyrimidin-3-ylamino)ethanol, 2-[(3-amino-pyrazolo [1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]-pyrimidine-3,7-diamine, 2,6-dimethylpyrazolo[1,5-a] pyrimidine-3,7-diamine, 2,5-N-7-N-7-tetramethy-pyrazolo [1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists, and the acid addition salts thereof.

Among the pyrazole derivatives, mention may be made more particularly of the compounds described in German patents DE 3,843,892, DE 4,133,957 and International patent applications WO 94/08969, WO 94/08970, French patent application FR-A-2,733,749 and German patent application DE 195 43 988, the disclosures of each of which are incorporated herein by reference, such as 4,5-diamino-1-methylpyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxy-methylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the acid addition salts thereof.

The oxidation base(s) preferably represent(s) from 0.0005 to 12% by weight approximately relative to the total weight of the ready-to-use dye composition according to the invention, and even more preferably from 0.005 to 6% by weight approximately relative to this weight.

The ammonia-generating 2-electron oxidoreductase-type enzymes that can be used in the ready-to-use dye composition according to the invention are defined by class E.C. 1.4.3 of enzyme nomenclature (see Enzyme Nomenclature, Academic Press Inc., 1989, the contents of which are incorporated herein by reference).

The enzymes can be chosen, in particular, from D-aspartate oxidases (E.C. 1.4.3.1.), L-amino acid oxidases (E.C. 1.4.3.2.), D-amino acid oxidases (E.C. 1.4.3.3.), (mono)amine oxidases containing a flavin (E.C. 1.4.3.4.), pyridoxamine phosphate oxidases (E.C. 1.4.3.5.), (di)amine oxidases containing copper (E.C. 1.4.3.6.), D-glutamate oxidases (E.C. 1.4.3.7.), ethanolamine oxidases (E.C. 1.4.3.8.), putrescine oxidases (E.C. 1.4.3.10.), L-glutamate oxidases (E.C. 1.4.3.11.), cyclohexylamine oxidases (E.C. 1.4.3.12.), protein-lysine-6-oxidases (E.C. 1.4.3.13.), L-lysine oxidases (E.C. 1.4.3.14.), D-glutamate (D-aspartate) oxidases (E.C. 1.4.3.15.), and L-aspartate oxidases (E.C. 1.4.3.16.).

According to a preferred embodiment of the invention, the ammonia-generating 2-electron oxidoreductase-type enzyme(s) is(are) chosen from the amino acid oxidase sub-classes, i.e., from classes E.C. 1.4.3.1, E.C. 1.4.3.2, E.C. 1.4.3.3,E.C. 1.4.3.7, E.C. 1.4.3.11, E.C. 1.4.3.14,E.C. 1.4.3.15 and E.C. 1.4.3.16.

The ammonia-generating 2-electron oxidoreductase(s) used in the ready-to-use dye composition according to the invention can be of animal, microbiological (bacterial, fungal or viral) or synthetic (obtained by chemical or biotechnological synthesis) origin.

The ammonia-generating 2-electron oxidoreductase(s) used in the ready-to-use dye composition according to the invention preferably represent(s) from 0.01 to 40% by weight approximately relative to the total weight of the ready-to-use dye composition, and even more preferably from 0.1 to 10% by weight approximately relative to this weight.

The enzymatic activity of the ammonia-generating 2-electron oxidoreductases used according to the invention can be defined from the oxidation of the donor under aerobic conditions. One unit U corresponds to the amount of enzyme which leads to the generation of 1 μmol of hydrogen peroxide per minute at a pH of 8.5 and at a temperature of 25° C.

Preferably, the amount of ammonia-generating 2-electron oxidoreductase(s) ranges from 10,000 to $4\times10^8$ units U approximately per 100 g of dye composition.

According to the invention, the term "donor" is intended to refer to the various substrate(s) required for the ammonia-generating 2-electron oxidoreductase used to function.

The nature of the donor (or substrate) for the enzyme varies as a function of the nature of the ammonia-generating 2-electron oxidoreductase that is used. Examples of donors for D-aspartate oxidases include D-aspartate and D-glutamate; examples of donors for L-amino acid oxidases include L-glycine, L-alanine, L-valine, L-phenylalanine and L-tryptophan; examples of donors for D-amino acid oxidases include D-alanine and D-phenylalanine; examples of donors for (mono)amine oxidases containing a flavin include benzylamine and octylamine; examples of donors for pyridoxamine phosphate oxidases include pyridoxine phosphate and pyridoxamine phosphate; examples of donors for (di)amine oxidases containing copper include 1,4-diaminobutane, 1,4-diaminopentane and spermidine; an example of a donor for D-glutamate oxidases includes D-glutamate; examples of donors for ethanolamine oxidases include monoethanolamine, 3-amino-1-propanol and 1-amino-2-propanol; an example of a donor for putrescine oxidase includes putrescinee; an example of a donor for L-glutamate oxidases includes L-glutamate; examples of donors for cyclohexylamine oxidases include cyclohexylamine and cycloamines; an example of a donor for protein-lysine-6-oxidases includes peptidyl-L-lysyl-peptide; examples of donors for L-lysine oxidases include L-lysine, L-ornithine, L-histidine, L-phenylalanine and L-arginine; examples of donors for D-glutamate (D-aspartate) oxidases include D-glutamate and D-aspartate; and finally, an example of a donor for L-aspartate oxidases includes L-aspartate.

The donor(s) (or substrate(s)) used according to the invention preferably represent(s) from 0.01 to 20% by weight approximately relative to the total weight of the ready-to-use dye composition in accordance with the invention, and even more preferably from 0.1 to 5% by weight approximately relative to this weight.

The ready-to-use dye composition according to the invention can also contain one or more couplers and/or one or more direct dyes, in particular, for modifying the shades, or for enriching them with glints.

Examples of the couplers that can be used in the ready-to-use dye compositions according to the invention include meta-phenylenediamines, meta-aminophenols, meta-diphenols and heterocyclic couplers, such as, for example, indole derivatives, indoline derivatives, benzimidazole derivatives, benzomorpholine derivatives, sesamol derivatives, pyridine, pyrimidine and pyrazole derivatives, and the acid addition salts thereof.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy4-methylpyridine, 1-H-3-methylpyrazol-5-one and 1-phenyl-3-methylpyrazol-5-one, and the acid addition salts thereof.

When they are present, the coupler(s) preferably represent(s) from 0.0001 to 10% by weight approximately relative to the total weight of the ready-to-use dye composition, and even more preferably from 0.005 to 5% by weight approximately relative to this weight.

In general, the acid addition salts that can be used in the context of the dye compositions of the invention (oxidation bases and couplers) are chosen, in particular, from the hydrochlorides, hydrobromides, sulphates, tartrates, lactates and acetates.

The medium suitable for dyeing (or support) for the ready-to-use dye composition according to the invention generally comprises water or a mixture of water and at least one organic solvent to dissolve the compounds that would not be sufficiently soluble in water. As organic solvents, examples include $C_1$–$C_4$ alkanols, such as ethanol and isopropanol; glycerol; glycols and glycol ethers, such as 2-butoxyethanol, propylene glycol, propylene glycol monomethyl ether, diethylene glycol monoethyl ether and monomethyl ether, and aromatic alcohols, such as benzyl alcohol or phenoxyethanol, similar products and mixtures thereof.

The solvents can be present in proportions preferably ranging from 1 to 40% by weight approximately relative to the total weight of the dye composition, and even more preferably ranging from 5 to 30% by weight approximately.

The pH of the ready-to-use composition according to the invention is chosen such that the enzymatic activity of the ammonia-generating 2-electron oxidoreductase is sufficient. It generally ranges from approximately 5 to approximately 11, and preferably from approximately 6.5 to approximately 10. It can be adjusted to the desired value through acidifying or basifying agents usually used in the dyeing of keratin fibers.

Among the acidifying agents, examples include inorganic or organic acids, such as hydrochloric acid, orthophosphoric acid, sulphuric acid, carboxylic acids, such as acetic acid, tartaric acid, citric acid and lactic acid, and sulphonic acid.

Among the basifying agents, examples include aqueous ammonia, alkaline carbonates, alkanolamines, such as mono-, di- and triethanolamine, 2-methyl-2-aminopropanol and derivatives thereof, sodium hydroxide, potassium hydroxide and the compounds of formula (IV) below:

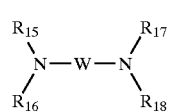

(IV)

in which W is a propylene residue optionally substituted with a hydroxyl group or a $C_1$–$C_4$ alkyl radical; $R_{15}$, $R_{16}$, $R_{17}$, and $R_{18}$, which may be identical or different, represent a hydrogen atom, a $C_1$–$C_4$ alkyl or $C_1$–$C_4$ hydroxyalkyl radical.

The ready-to-use dye composition according to the invention can also contain various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the ammonia-generating 2-electron oxidoreductase used in accordance With the invention, such as, for example, peroxidases, penetrating agents, sequestering agents, fragrances, buffers, dispersants, conditioners, such as, for example, volatile or nonvolatile silicones, which may or may not be modified, film-forming agents, ceramides, preserving agents and opacifiers.

Needless to say, persons skilled in the art will take care to select this or these optional complementary compound(s) such that the advantageous properties intrinsically associated with the ready-to-use dye composition according to the invention are not, or are not substantially, adversely affected by the addition(s) envisaged.

The ready-to-use dye composition according to the invention can be in various forms, such as in the form of liquids, creams or gels, optionally pressurized, or in any other form suitable for dyeing keratin fibers, and, in particular, human hair. In the case where the oxidation dye(s) and the ammonia-generating 2-electron oxidoreductase(s) are packaged together as a ready-to-use composition, the packaged composition should be free of oxygen gas, so as to avoid any premature oxidation of the oxidation dye(s).

A subject of the invention is also a process for the oxidation dyeing of keratin fibers, and, in particular, human keratin fibers, such as the hair, using the ready-to-use dye composition as defined above.

According to this process, at least one ready-to-use dye composition as defined above is applied to the fibers, for a period sufficient to develop the desired coloration, after which the fibers are rinsed, optionally washed with shampoo, rinsed again and dried.

The time required to develop the coloration on the keratin fibers generally ranges from 3 to 60 minutes, and even more precisely ranges from 5 to 40 minutes.

According to another specific embodiment of the invention, the process includes a first step, which comprises separately storing, on the one hand, a composition (A) comprising, in a medium suitable for dyeing, at least one oxidation base and, on the other hand, a composition (B) containing, in a medium suitable for dyeing, at least one ammonia-generating 2-electron oxidoreductase-type enzyme, the composition (A) and/or the composition (B) containing at least one donor for the enzyme, and then in mixing them together at the time of use, before applying this mixture to the keratin fibers.

Another subject of the invention is a multi-compartment dyeing device or "kit" or any other multi-compartment packaging system, a first compartment of which contains composition (A) as defined above and a second compartment of which contains composition (B) as defined above. These devices can be equipped with a means for applying the desired mixture to the hair, such as the devices described in French patent FR-2,586,913, the disclosure of which is incorporated herein by reference, in the name of L'Oréal.

The present invention is further illustrated by the following examples which are designed to teach those of ordinary skill in the art how to practice the invention. The following examples are merely illustrative of the invention and should not be construed as limiting the invention as claimed.

EXAMPLES

Dyeing Examples 1 and 2

The ready-to-use dye compositions according to the invention below were prepared:

| COMPOSITION | 1 | 2 |
|---|---|---|
| para-Phenylenediamine (oxidation base) | 0.324 g | — |
| para-Aminophenol (oxidation base) | — | 0.327 g |
| 1-Amino-2-methoxy-4,5-methylene-dioxybenzene (coupler) | 0.611 g | — |
| 2-Methyl-5-aminophenol (coupler) | — | 0.369 g |
| D-Alanine oxidase, sold by the company Sigma (reference A1614) (enzyme in accordance with the invention) | 20,000 U | — |
| D-Alanine oxidase, sold by the company Sigma (reference A1914) (enzyme in accordance with the invention) | — | 20,000 U |
| D-Alanine (donor) | 0.535 g | 0.535 g |
| 2-Amino-2-methyl-1-propanol q.s. pH | 9 | 9 |
| Demineralized water q.s.p. | 100 g | 100 g |

Each of the ready-to-use dye compositions described above was applied to locks of natural gray hair containing 90% white hairs for 30 minutes at room temperature. The hair was then rinsed, washed with a standard shampoo and then dried.

The hair was dyed in the shade shown in the table below:

| EXAMPLE | SHADE OBTAINED |
|---|---|
| 1 | golden matt ash |
| 2 | golden |

Comparative Dyeings Examples 3 and 4

The ready-to-use dye compositions below were prepared:

| COMPOSITION | 3 | 4(*) |
|---|---|---|
| para-Phenylenediamine (oxidation base) | 0.324 g | 0.324 g |
| 2-Methyl-5-aminophenol (coupler) | 0.369 g | 0.369 g |
| D-Alanine oxidase, solid by the company Sigma (reference A 1614) (enzyme in accordance with the invention) | 20,000 U | — |
| D-Alanine (donor) | $3.10^{-3}$ mol | — |
| Uricase from *Arthrobacter globiformis* at a concentration of 20 I.U./mg, sold by the company Sigma | — | 20,000 U |
| Uric acid | — | $3.10^{-3}$ mol |
| 2-Amino-2-methyl-1-propanol q.s. pH | 9.75 ± 0.25 | 9.75 ± 0.25 |
| Demineralized water q.s.p. | 100 g | 100 g |

(*)Comparative example which does not form part of the invention

Each of the ready-to-use dye compositions described above was applied to locks of natural gray hair containing 90% white hairs for 30 minutes at room temperature. The hair was then rinsed, washed with a standard shampoo and then dried.

The color of the locks was evaluated before and after the dyeing, in the system L* a* b*, by means of a MINOLTA® CM 2002 spectrophotometer (Illuminant D65).

In the system L* a* b*, the three parameters denote, respectively, the intensity (L*), the shade (a*) and the saturation (b*).

According to this system, the higher the value of L, the lighter or less intense the color. Conversely, the lower the value of L, the darker or more intense the color.

a* and b* indicate two color axes, a* indicates the green/red color axis and b* indicates the blue/yellow color axis. Values close to 0 for a* and b* correspond to gray shades.

The rise in the coloration (ΔE) can be calculated by applying the following equation:

$$\Delta E = \sqrt{(L^* - L_0^*)^2 + (a^* - a_0^*)^2 + (b^* - b_0^*)^2}$$

In this equation, ΔE represents the difference in color between two locks (in the present case the rise in the coloration), L*, a* and b* represent, respectively, the intensity, the shade and the saturation of the dyed lock, $L_0^*$, $a_0^*$ and $b_0^*$ representing, respectively, the intensity, the shade and the saturation of the undyed lock.

The higher the value of ΔE, the greater the difference in color between the two locks, and in the present case, the greater the rise in the coloration.

For each of the compositions tested, the coloration difference ΔE between the undyed locks and the dyed locks was calculated according to the formula indicated above, so as to be able to evaluate the intensity of the coloration.

The results obtained are shown in the table below:

| Example | Color of the undyed lock | | | Color of the dyed lock | | | Intensity of the coloration (ΔE) |
|---|---|---|---|---|---|---|---|
| | L* | a* | b* | L* | a* | b* | |
| 3 | 54 | 1 | 12 | 27 | 13 | 3 | 31 |
| 4* | 54 | 1 | 12 | 31 | 13 | 4 | 26 |

These results show that the composition of Example 3 according to the invention, i e., containing D-alanine oxidase, an ammonia-generating 2-electron oxidoreductase, in the presence of D-alanine as a donor, led to a more intense coloration than the composition of Example 4 according to the prior art, containing uricase, which was not an ammonia-generating 2-electron oxidoreductase, and uric acid as a donor.

The foregoing written description relates to various embodiments of the present invention. Numerous changes and modifications may be made therein without departing from the spirit and scope of the invention as defined in the following claims.

What is claimed is:

1. A ready-to-use composition for the oxidation dyeing of keratin fibers, comprising:
    at least one oxidation base,
    at least one ammonia-generating 2-electron oxidoreductase-type enzyme,
    and at least one donor for said at least one enzyme.

2. A composition according to claim 1, wherein said keratin fibers are human keratin fibers.

3. A composition according to claim 2, wherein said human keratin fibers are human hair.

4. A composition according to claim 1, wherein said composition is in a medium suitable for dyeing.

5. A composition according to claim 1, wherein said at least one oxidation base is chosen from para-phenylenediamines, double bases, para-aminophenols, ortho-aminophenols and heterocyclic oxidation bases.

6. A composition according to claim 5, wherein said para-phenylenediamines are chosen from the compounds of formula (I), and acid addition salts thereof:

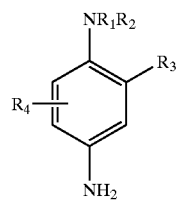

(I)

wherein:

$R_1$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical, a $C_1$–$C_4$ alkyl radical substituted with a nitrogenous group, a phenyl radical and a 4'-aminophenyl radical;

$R_2$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical and a $C_1$–$C_4$ alkyl radical substituted with a nitrogenous group;

$R_3$ is chosen from a hydrogen atom, a halogen atom, a $C_1$–$C_4$ alkyl radical, a $C_1$–$C_4$ monohydroxyalkyl radical, a $C_1$–$C_4$ hydroxyalkoxy radical, an acetylamino$(C_1$–$C_4)$alkoxy radical, a $C_1$–$C_4$ mesylaminoalkoxy radical and a carbamoylamino$(C_1$–$C_4)$alkoxy radical, $R_4$ is chosen from a hydrogen atom, a halogen atom and a $C_1$–$C_4$ alkyl radical.

7. A composition according to claim 6, wherein in said $R_3$, said halogen atom is chosen from chlorine, bromine, iodine and fluorine atoms.

8. A composition according to claim 6, wherein said para-phenylenediamines of formula (I) are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediarnine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-miethylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid addition salts thereof.

9. A composition according to claim 5, wherein said double bases are chosen from compounds of formula (II), and acid addition salts thereof:

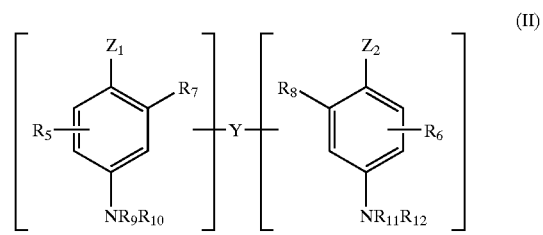

(II)

wherein:

$Z_1$ and $Z_2$, which are identical or different, are chosen from a hydroxyl radical and an —$NH_2$ radical wherein said $NH_2$ radical is unsubstituted or substituted with a $C_1$–$C_4$ alkyl radical or with a linker arm Y;

linker arm Y is a linear or branched alkylene chain containing from 1 to 14 carbon atoms, which is optionally interrupted by or terminated with at least one of one or more nitrogenous groups and one or more hetero atoms, and optionally substituted with one or more hydroxyl or $C_1$–$C_6$ alkoxy radicals;

$R_5$ and $R_6$ are chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical and a linker arm Y;

$R_7$, $R_8$, $R_9$, $R_{10}$, $R_{11}$ and $R_{12}$, which are identical or different, are chosen from a hydrogen atom, a linker arm Y and a $C_1$–$C_4$ alkyl radical;

with the proviso that said compounds of formula (II) contain only one linker arm Y per molecule.

10. A composition according to claim 9, wherein in said linker arm Y, said hetero atoms are chosen from oxygen, sulphur and nitrogen atoms.

11. A composition according to claim 9, wherein said double bases of formula (II) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetra-methylenediamine, N,N'-bis(ethyl)-N,N'bis(4'-amino-3'-methylphenyl)ethylenediamine, 1,8-bis(2,5-diaminophenoxy)-3,5-dioxaoctane, and acid addition salts thereof.

12. A composition according to claim 5, wherein said para-aminophenols are chosen from compounds of formula (III), and acid addition salts thereof:

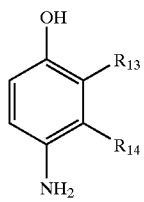

(III)

wherein:

$R_{13}$ is chosen from a hydrogen atom, a halogen atom, a $C_1$–$C_4$ alkyl radical, a $C_1$–$C_4$ monohydroxyalkyl radical, a ($C_1$–$C_4$)alkoxy($C_1$–$C_4$)alkyl radical, a $C_1$–$C_4$ aminoalkyl radical and a hydroxy($C_1$–$C_4$)alkylamino ($C_1$–$C_4$)alkyl radical, $R_{14}$ is chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical, a $C_1$–$C_4$ cyanoalkyl radical and a ($C_1$–$C_4$)alkoxy($C_1$–$C_4$)alkyl radical, with the proviso that at least one of the radicals $R_{13}$ or $R_{14}$ is a hydrogen atom.

13. A composition according to claim 12, wherein said para-aminophenols of formula (III) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

14. A composition according to claim 5, wherein said ortho-aminophenols are chosen from 2-aminophenol, 2-amino-5-methylphenol, 2-amino-6-methylphenol, 5-acetamido-2-aminophenol, and acid addition salts thereof.

15. A composition according to claim 5, wherein said heterocyclic bases are chosen from pyridine derivatives, pyrimidine derivatives, pyrazole derivatives, and acid addition salts thereof.

16. A composition according to claim 1, wherein said at least one oxidation base is present in an amount ranging from 0.0005 to 12% by weight relative to the total weight of the ready-to-use dye composition.

17. A composition according to claim 1, wherein said at least one ammonia-generating 2-electron oxidoreductase-type enzyme is chosen from D-aspartate oxidases, L-amino acid oxidases, D-amino acid oxidases, (mono)amine oxidases containing a flavin, pyridoxamine phosphate oxidases, (di)amine oxidases containing copper, D-glutamate oxidases, ethanolamine oxidases, putrescine oxidases, L-glutamate oxidases, cyclohexylamine oxidases, protein-lysine-6-oxidases, L-lysine oxidases, D-glutamate (D-aspartate) oxidases and L-aspartate oxidases.

18. A composition according to claim 1, wherein said at least one ammonia-generating 2-electron oxidoreductase is present in an amount ranging from 0.01 to 40% by weight relative to the total weight of the ready-to-use dye composition.

19. A composition according to claim 1, wherein said at least one donor for said at least one enzyme is present in an amount ranging from 0.01 to 20% by weight relative to the total weight of the ready-to-use dye composition.

20. A composition according to claim 1, further comprising at least one coupler.

21. A composition according to claim 1, further comprising at least one direct dye.

22. A composition according to claim 20, wherein said at least one coupler is chosen from meta-phenylenediamines, meta-aminophenols, meta-diphenols, heterocyclic couplers, and acid addition salts thereof.

23. A composition according to claim 22, wherein said at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazole-5-one, 1-phenyl-3-methylpyrazol-5-one, and acid addition salts thereof.

24. A composition according to claim 20, wherein said at least one coupler is present in an amount ranging from 0.0001 to 10% by weight relative to the total weight of the ready-to-use dye composition.

25. A composition according to claim 6, wherein said acid addition salts are chosen from hydrochlorides, hydrobromides, sulphates, tartrates, lactates and acetates.

26. A composition according to claim 8, wherein said acid addition salts are chosen from hydrochlorides, hydrobromides, sulphates, tartrates, lactates and acetates.

27. A composition according to claim 9, wherein said acid addition salts are chosen from hydrochlorides, hydrobromides, sulphates, tartrates, lactates and acetates.

28. A composition according to claim 11, wherein said acid addition salts are chosen from hydrochlorides, hydrobromides, sulphates, tartrates, lactates and acetates.

29. A composition according to claim 12, wherein said acid addition salts are chosen from hydrochlorides, hydrobromides, sulphates, tartrates, lactates and acetates.

30. A composition according to claim 13, wherein said acid addition salts are chosen from hydrochlorides, hydrobromides, sulphates, tartrates, lactates and acetates.

31. A composition according to claim 14, wherein said acid addition salts are chosen from hydrochlorides, hydrobromides, sulphates, tartrates, lactates and acetates.

32. A composition according to claim 15, wherein said acid addition salts are chosen from hydrochlorides, hydrobromides, sulphates, tartrates, lactates and acetates.

33. A composition according to claim 22, wherein said acid addition salts are chosen from hydrochlorides, hydrobromides, sulphates, tartrates, lactates and acetates.

34. A composition according to claim 23, wherein said acid addition salts are chosen from hydrochlorides, hydrobromides, sulphates, tartrates, lactates and acetates.

35. A method of oxidation dyeing of keratin fibers, comprising applying at least one ready-to-use dye composition to said keratin fibers for a period of time sufficient to develop a desired coloration, wherein said at least one ready-to-use composition comprses:

at least one oxidation base, at least one ammonia-generating 2-electron oxidoreductase-type enzyme, and at least one donor for said at least one enzyme.

36. A method according to claim 35, wherein said keratin fibers are human keratin fibers.

37. A method according to claim 36, wherein said human keratin fibers are human hair.

38. A method according to claim 35, wherein said period of time sufficient to develop a desired coloration on said keratin fibers ranges from 3 to 60 minutes.

39. A method according to claim 35, further comprising, before said application, separately storing said at least one oxidation base, and said at least one enzyme, wherein said at least one donor for said at least one enzyme is stored either with said at least one oxidation base or with said at least one enzyme, and mixing together said separately stored ingredients before said application to said keratin fibers.

40. A multi-compartment device for oxidation dyeing of keratin fibers, comprising at least two compartments, wherein a first compartment comprises a first composition comprising at least one oxidation base;

a second compartment comprises a second composition comprising at least one ammonia-generating 2-electron oxidoreductase-type enzyme;

one of the first composition and the second composition comprises at least one donor for said at least one enzyme; and said first composition and said second composition are mixed prior to the oxidation dyeing of keratin fibers.

41. A composition according to claim 1, wherein said composition is a pre-mixed composition.

42. A composition according to claim 1, wherein said composition is pre-mixed prior to the oxidation dyeing of keratin fibers.

43. A composition according to claim 1, wherein said composition is packaged free of oxygen gas.

44. A method according to claim 35, wherein composition is a pre-mixed composition.

45. A method according to claim 35, wherein said composition is pre-mixed prior to the oxidation dyeing of keratin fibers.

46. A method according to claim 35, wherein said composition is packaged free of oxygen gas.

* * * * *

UNITED STATES PATENT AND TRADEMARK OFFICE
CERTIFICATE OF CORRECTION

PATENT NO. : 6,685,750 B1
DATED : February 3, 2004
INVENTOR(S) : Grégory Plos et al.

It is certified that error appears in the above-identified patent and that said Letters Patent is hereby corrected as shown below:

Column 12,
Line 30, "N,N-diethyl-para-phenylenediarnine," should read -- N,N-diethyl-para-phenylenediamine, --.
Lines 32-33, "4-N,N-bis(β-hydroxyethyl)amino-2-miethylaniline," should read -- 4-N,N-bis(β-hydroxyethyl)amino-2-methylaniline, --.

Column 13,
Lines 23-24, "N,N'-bis (ethyl)-N,N'bis(4'-amino-3'-methylphenyl)ethylenediamine," should read -- N,N'-bis(ethyl)-N,N'-bis(4'-amino-3'-methylphenyl)ethylenediamine, --.

Signed and Sealed this

Fifteenth Day of June, 2004

JON W. DUDAS
*Acting Director of the United States Patent and Trademark Office*